United States Patent [19]

Heveling et al.

[11] Patent Number: 5,698,607
[45] Date of Patent: Dec. 16, 1997

[54] TERTIARY DIAMINE, ITS USE AS CATALYST, AND PROCESS FOR PREPARING TERTIARY DIAMINES

[75] Inventors: Josef Heveling, Naters; Andreas Gerhard, Visp; Ulrich Daum, Hofstetten, all of Switzerland

[73] Assignee: Lonza AG, Gampel/Valais, Switzerland

[21] Appl. No.: 737,309

[22] PCT Filed: May 10, 1995

[86] PCT No.: PCT/EP95/01773

§ 371 Date: Jan. 30, 1997

§ 102(e) Date: Jan. 30, 1997

[87] PCT Pub. No.: WO95/30666

PCT Pub. Date: Nov. 16, 1995

[30] Foreign Application Priority Data

May 10, 1994 [CH] Switzerland .................. 1460/94

[51] Int. Cl.$^6$ .................................................. C07D 401/06
[52] U.S. Cl. .................. 521/129; 524/839; 528/44; 540/596; 546/184; 546/186; 548/524; 553/459
[58] Field of Search ..................... 524/839; 528/44; 540/596; 546/184, 186; 548/524; 558/459; 521/129

[56] References Cited

U.S. PATENT DOCUMENTS

| | | | |
|---|---|---|---|
| 3,673,251 | 6/1972 | Frampton et al. | 564/469 |
| 3,728,284 | 4/1973 | Reynolds | 502/243 |
| 3,787,496 | 1/1974 | Whitney et al. | 564/405 |
| 3,886,193 | 5/1975 | Whitney et al. | 556/70 |
| 3,898,286 | 8/1975 | Drake | 564/491 |
| 4,521,602 | 6/1985 | Rebafka et al. | 546/184 |
| 4,885,391 | 12/1989 | Herkes | 564/491 |
| 5,091,064 | 2/1992 | Meinert et al. | 205/430 |
| 5,120,731 | 6/1992 | Meinert et al. | 514/231.5 |
| 5,173,512 | 12/1992 | Meinert et al. | 514/231.2 |
| 5,260,496 | 11/1993 | Meinert et al. | 570/179 |

FOREIGN PATENT DOCUMENTS

| | | |
|---|---|---|
| 415263 | 8/1990 | European Pat. Off. |
| 1032920 | 12/1958 | Germany . |
| 1034180 | 12/1958 | Germany . |
| 838652 | 6/1960 | United Kingdom . |

OTHER PUBLICATIONS

Laine, R.M. et al, "Catalytic Reactions of Pyridine with CO and H2O. Reduction of CO to Hydrocarbon. Applications of the Water–Gas Shift Reaction." J. Org. Chem. 1979, 44(26), pp. 4964–4966.

Primary Examiner—C. Warren Ivy
Assistant Examiner—Garth M. Dahlen
Attorney, Agent, or Firm—Fisher, Christen & Sabol

[57] ABSTRACT

Tertiary diamines having two saturated heterocyclic rings joined by an aliphatic carbon chain, of the general formula

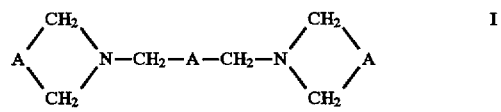

in which each A is a two- to four-membered aliphatic carbon chain substituted if desired by one or more $C_1$–$C_4$-alkyl groups, are prepared in one stage by catalytic hydrogenation of the corresponding dinitriles of the general formula $$N\equiv C-A-C\equiv N \qquad II$$

The diamines preparable in accordance with the invention are particularly suitable as catalysts for the production of polyurethanes.

16 Claims, No Drawings

TERTIARY DIAMINE, ITS USE AS CATALYST, AND PROCESS FOR PREPARING TERTIARY DIAMINES

This application is a 371 of PCT/EP95/01773 filed May 10, 1995.

BACKGROUND OF THE INVENTION

1. Field of the Invention

Tertiary diamine, its use as catalyst, and process for preparing tertiary diamines The present invention relates to a process for preparing tertiary diamines having two saturated heterocyclic rings of aliphatic dinitriles, which rings are connected by an aliphatic carbon chain, and to a novel tertiary diamine and its use as a catalyst for the preparation of polyurethanes.

Tertiary diamines, for example 1,5-dipiperidino-pentane, are valuable compounds owing to their high basicity and relatively low volatility and can be employed, for example, as hardeners in epoxy resins (German Patent No. C10 32 920).

2. Background of the Invention

A relatively new use of such compounds is as starting material for the preparation of emulsion stabilizers for blood substitutes (European Published Patent Application No. A 0 415 263).

The preparation processes known to date for these compounds (see for example European Published Application No. A 0 415 263, p. 8) generally require two different starting substances and in some cases produce unwanted waste products (salts) and in some cases give unsatisfactory yields. Also known are processes in which, for example, piperidine is reacted under the influence of a catalyst to form 1,5-dipiperidinopentane (German Patent No. C10 34 180). These processes too often give rise to only poor yields.

BROAD DESCRIPTION OF THE INVENTION

It was therefore an object of the present invention to provide a simple process which gives tertiary diamines having two saturated heterocyclic rings, connected by an aliphatic carbon chain, in good yield without the production of relatively large quantities of waste products.

This object is achieved in accordance with the invention by the process.

It has surprisingly been found that tertiary diamines of the general formula

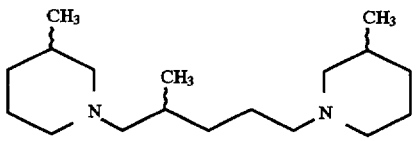

in which each A is identical and is a two- to four-membered aliphatic carbon chain, and which may if desired be substituted by one or more $C_1$–$C_4$-alkyl groups, can be prepared in one stage by hydrogenating the corresponding aliphatic dinitriles of the general formula

in which A is as defined above. A by-product of this process is 4 mol of ammonia per mole of diamine.

The hydrogenation is expediently carried out at a temperature of 100°–250° C. and under elevated pressure in the presence of a supported palladium catalyst.

As supported palladium catalyst it is preferred to employ palladium on alumina. Good results have been obtained with relatively low palladium contents of, for example, 1%.

The hydrogen pressure in the course of the hydrogenation is preferably greater than 10 bar and is, for example, about 50 bar. The reaction temperature established is preferably a temperature from 150° to 220° C., for example 180° C.

The hydrogenation is preferably carried out continuously. For this purpose, the dinitrile is passed over the catalyst together with hydrogen in a suitable reactor.

A suitable carbon chain A is preferably 1,2-ethanediyl, 1,3-propanediyl, 1,4-butanediyl or 1,3-butanediyl (≡1-methyl-1,3-propanediyl), corresponding to the dinitriles succinonitrile, glutaronitrile, adiponitrile or 2-methylglutaronitrile.

To the dinitrile II it is possible to add up to twice the molar quantity of the corresponding cyclic amine

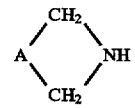

in which A is as defined above, i.e. addition up to a molar ratio of II to III of 1:2, the amine III being incorporated into the product I. This has the advantage that it is possible by this means to recycle the cyclic amine III, which is also formed in the novel process as a by-product, and ultimately to convert it into the desired product I.

Preferably, 3-methylpiperidine is employed as cyclic amine II and 2-methylglutaronitrile as dinitrile II.

A particularly preferred starting material is 2-methylglutaronitrile, which as novel product gives 1,5-bis(3-methylpiperidino)-2-methylpentane of the formula

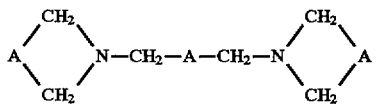

This compound is particularly suitable as a catalyst for the preparation of polyurethanes, polyurethane/polyurea mixtures and polyureas. Using this catalyst, the polymers can be prepared both as elastomers and in the form of foams.

The examples which follow illustrate the implementation of the novel process.

The hydrogen streams are based on standard conditions, and the throughput is in each case indicated in g of starting material per g of catalyst per hour. The composition of each product was determined by gas chromatography.

DETAILED DESCRIPTION OF THE INVENTION

EXAMPLE 1

3 g of a Pd/Al$_2$O$_3$ catalyst (1% Pd, particle size 0.315–1 mm) were placed in a reactor (13 mm ⌀). In the stream of hydrogen (120 ml/min), a temperature of 180° C. and a pressure of 50 bar were established. Then 99.8% pure 2-methylglutaronitrile (MGN) was metered in. The throughput was 2.1 g/(g·h), and the molar ratio of MGN to H$_2$ was 1:5. With complete conversion, the concentrations in the product stream after a reaction period of 40 h were found (GC) to be as follows: 82.5% 1,5-bis(3-methylpiperidino)-2-methylpentane, 0.4% isomer mixture of 2-methyl-5-(3-methylpiperidino)pentanenitrile (major component) and 4-methyl-5-(3-methylpiperidino)pentanenitrile, 8.4% 3-methylpiperidine, remainder: 8.7%. The product mixture was water-clear.

EXAMPLE 2

3 g of a Pd/MgCl$_2$Al$_2$O$_3$ catalyst (particle size 0.315–1 mm) containing 1% Pd and 1.2% Mg were placed in a reactor (13 mm ∅). In the stream of hydrogen (120 ml/min), a temperature of 170° C. and a pressure of 50 bar were established. Then 99.8% pure 2-methylglutaronitrile (MGN) was metered in. The throughput was 2.1 g/(g·h). With complete conversion, the concentrations in the product stream after a reaction period of 22 h were found (GC) to be as follows: 78.4% 1,5-bis(3-methylpiperidino)-2-methylpentane, 8.3% isomer mixture of 2-methyl-5-(3-methylpiperidino)pentanenitrile (major component) and 4-methyl-5-(3-methylpiperidino)pentanenitrile, 3.0% 3-methylpiperidine, remainder: 10.3%. The product mixture was water-clear.

EXAMPLE 3

3 g of a Pd/MgCl$_2$Al$_2$O$_3$ catalyst (particle size 0.315–1 mm) containing 1% Pd and 1.2% Mg were placed in a reactor (13 mm ∅). In the stream of hydrogen (120 ml/min), a temperature of 190° C. and a pressure of 50 bar were established. Then 99.8% pure 2-methylglutaronitrile (MGN) was metered in. The throughput was 2.1 g/(g·h). With complete conversion, the concentrations in the product stream were found (GC) to be as follows: 76.3% 1,5-bis(2-methyl-piperidino)-2-methylpentane, 4.3% of 2-methyl-5-(3-methylpiperidino)pentanenitrile, 15.3% 3-methylpiperidine, remainder: 4.1% (reaction time: 90 h). The water-clear product was distilled, and 1,5-bis(3-methylpiperidino)-2-methylpentane was obtained in a purity of 99.5% (108° C./1.3 mbar).

Analytical data:

1,5-bis(3-methylpiperidino)-2-methylpentane:

C$_{18}$H$_{36}$N$_2$ calculated: C 77.1 H 12.9 N 10.0 found: C 77.2 H 13.4 N 10.0

Molar mass 280 (MS)

| $^1$H—NMR (CDCl$_3$, 400 MHz) δ: | 2.65–2.90(m, 4H, ring-N—CH$_2$); 2.25(t, 2H, N—CH$_2$—CH$_2$); 2.02 (m, 2H, N—CH$_2$—CH): 1.34–1.82(m, 16H); 0.78–1.08(m, 12H, CH$_3$ etc.). |
|---|---|
| (Diastereomer mixture) | |
| $^{13}$C—NMR (CDCl$_3$, 100 MHz) δ: | 54.1–66.3(N—CH$_2$); 33.3 (N—CH$_2$—CH$_2$—CH$_2$); 30.5–31.2(CH; 24.5–25.7 (N—CH$_2$—CH$_2$); 18.5–19.9 (CH$_3$). |

| $^1$H—NMR (CDCl$_3$, 400 MHz) δ: | 1.40–2.85(m, 16H, CH+ CH$_2$); 1.32(d, 3H, CH$_3$— |
|---|---|
| (Major component) | |

| | CH—CN); 0.86(d, 3H, ring-CH$_3$). |
|---|---|
| $^{13}$C—NMR (CDCl$_3$, 100 MHz) δ: | 123.01(s); 62.20(t); 58.28(t); 54.12(t); 33.13(t); 32.23(t); 31.19(d); 25.62(t); 25.47(d); 24.41(d); 19.77(g); 18.07(q). |
| (Main component) | |

EXAMPLES 4–7

Use of 1,5-bis(3-methylpiperidino)-2-methylpentane as polyurethane catalyst:

Abbreviations:

VL: Desmodur® VL from Bayer, aromatic diisocyanate containing about 32% -NCO

D550U: Desmophen® 550U, polypropylene glycol from Bayer, trifunctional with 10.5%-OH DBU: Diazabicyclo[5.4.0]undec-7-ene BMPMP: 1,5-bis(3-methylpiperidino)-2-methylpentane DBU was used as comparison catalyst. Desmophen was placed together with the amine (DBU or BMPMP) and thorough mixing was carried out to give a solution. In Example 6 and 7, water was added as well, giving an emulsion/solution. A weighed quantity of isocyanate (VL) was added with vigorous stirring at time t=0. A note was made of the points in time at which the solution is no longer cloudy,
marked heating can be detected,
the mixture becomes solid.

The results (BMPMP in comparison with DBU) are evident from Table 1.

The addition of water in Examples 6 and 7 brings about partial hydrolysis of the isocyanate to the corresponding amine and the evolution of CO$_2$. The corresponding amine reacts with the remaining isocyanate to form a urea compound, while the CO$_2$ acts as blowing agent in the formation of foam.

TABLE 1

| Example No. | t[s] no longer cloudy | t[s] heating | t[s] solid | VL [g] | D550U [g] | DBU [g] | BMPMP [g] | H$_2$O [g] | Volume [ml] | Notes (colour etc.) |
|---|---|---|---|---|---|---|---|---|---|---|
| 4 | 60 | 62 | 90 | 50.0 | 55.0 | 0.5 | — | — | | brown, clear hard |
| 5 | 70 | 90 | 360 | 50.0 | 55.0 | — | 0.5 | — | | ochre, hard foam |
| 6 | 200 | 200 | 1200 | 50.0 | 45.0 | 0.1 | — | 0.5 | 450 | ochre, foam |
| 7 | 210 | 210 | 900 | 50.0 | 45.0 | — | 0.1 | 0.5 | 450 | ochre, foam |

EXAMPLE 8

Investigation regarding the reaction mechanism:

3 g of a Pd/Al$_2$O$_3$ catalyst (1% Pd, particle size 0.315–1 mm) were placed in a reactor (13 mm ∅). In the stream of hydrogen (120 ml/min) a temperature of 180° C. and a pressure of 50 bar were established. Then 99.8% pure 2-methylglutaronitrile (MGN) was metered in. The throughput was 2.1 g/(g·h). With complete conversion, the concentrations (GC) established in the product stream after a reaction period of 6 h were as follows: 78% 1,5-bis(3-methylpiperidino)-2-methylpentane, 21% 3-methylpiperidine (MPI), remainder: 1%. Subsequently, 3-methylpiperidine (MPI) instead of 2-methylglutaronitrile (MGN) was passed over the catalyst. >99.5% of the MPI passed over the catalyst unchanged. Then MPI and MGN in a molar ratio of 2:1 were passed over the catalyst. The concentrations (GC) established in the product stream were as follows: 18.9% MPI, 70.6% 1,5-bis(3-methylpiperidino)-2-methylpentane, remainder: 10.5%. The experimental results show that MPI alone is not converted to 1,5-bis(3-methylpiperidino)-2-methylpentane. However, when added to MGN, MPI is incorporated into the desired product.

EXAMPLE 9

3 g of a Pd/Al$_2$O$_3$ catalyst (1% Pd, particle size 0.315–1 mm) were placed in a reactor (13 mm Ø). In the stream of hydrogen (140 ml/min) a temperature of 180° C. and a pressure of 50 bar were established. Then glutaronitrile was metered in. The throughput was 2.1 g/(g·h). At a conversion of 98.6%, the product stream contained, after a reaction period of 4 h, 34.6% 5-piperidinopentanenitrile, 32.4% 1,5-dipiperidinopentane and 5.5% piperidine (GC).

EXAMPLE 10

3 g of a Pd/Al$_2$O$_3$ catalyst (1% Pd, particle size 0.315–1 mm) were placed in a reactor (13 mm ø). In the stream of hydrogen (120 ml/min) a temperature of 180° C. and a pressure of 50 bar were established. Then adiponitrile was metered in. The throughput was 2.1 g/(g·h). At a conversion of 98.8%, the product stream contained, after a reaction period of 3 h, 26% 6-(hexahydro-1H-azepin-1-yl) hexanenitrile, 20% 1,6-bis(hexahydro-1H-azepin-1-yl) hexane and 13% hexahydro-1H-azepine (GC).

EXAMPLE 11–13

3 g of a Pd/Al$_2$O$_3$ catalyst (1% Pd, particle size 0.315–1.0 mm) were placed in a reactor (13 mm ø). In the stream of hydrogen (120 ml/min), the reactor was heated at 50 bar to 180° C.. Then the metered addition of 99.8% pure 2-methylglutaronitrile was begun. The molar ratio of MGN to H$_2$ and the MGN throughput were varied and the following results were obtained.

EXAMPLE 11

MGN:H$_2$=1:10

Throughput: 2.10 g/(g·h)

| Product composition | |
| --- | --- |
| 1,5-Bis(3-methylpiperidino)-2-methylpentane | 71.2% |
| 2(4)-Methyl-5-(3-methylpiperidino)pentanenitrile | 0.7% |
| 2-Methylglutaronitrile | 0% |
| 3-Methylpiperidine | 9.2% |
| Remainder | 18.9% |

EXAMPLE 12

MGN:H$_2$=1:3.4

Throughput: 2.10 g/g·h)

| Product composition | |
| --- | --- |
| 1,5-Bis(3-methylpiperidino)-2-methylpentane | 44.2% |
| 2(4)-Methyl-5-(3-methylpiperidino)pentanenitrile | 20.1% |
| 2-Methylglutaronitrile | 8.4% |
| 3-Methylpiperidine | 3.6% |
| Remainder | 23.7% |

EXAMPLE 13

MGN:H$_2$=1:5

Throughput: 1.73 g/(g·h)

| Product composition | |
| --- | --- |
| 1,5-Bis(3-methylpiperidino)-2-methylpentane | 80.4% |
| 2(4)-Methyl-5-(3-methylpiperidino)pentanenitrile | 3.6% |
| 2-Methylglutaronitrile | 0% |
| 3-Methylpiperidine | 5.7% |
| Remainder | 10.2% |

Examples 1 and 11–13 show that the highest selectivity for the formation of the bis(methylpiperidino) compound is reached at a molar ratio of MGN to H$_2$ of approximately 1:5.

We claim:

1. Process for preparing tertiary diamines of the general formula

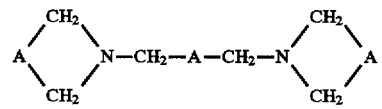

in which each A is a two- to four-membered aliphatic carbon chain, which is unsubstituted or substituted by one or more C$_1$–C$_4$-alkyl groups, characterized in that a dinitrile of the general formula

   II in which A is as defined above is reacted with hydrogen with a reaction temperature of 100°–250° C. under elevated pressure in the presence of a supported palladium catalyst.

2. Process according to claim 1, characterized in that the supported palladium catalyst employed is palladium on alumina.

3. Process according to claim 2, characterized in that the hydrogen pressure is greater than 10 bar.

4. Process according to claim 3, characterized in that the reaction temperature is 150° to 220° C.

5. Process according to claim 4, characterized in that the reaction with hydrogen is carried out continuously.

6. Process according to claim 5, characterized in that the dinitrile (II) which is employed is succinonitrile, glutaronitrile, adiponitrile or 2-methylglutaronitrile.

7. Process according to claim 6, characterized in that, to the dinitrile II, there is added the corresponding cyclic amine of the general formula:

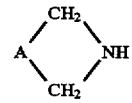   III in which A is as defined in claim 1 in a quantity of up to 2 mol per mol of dinitrile.

8. Process according to claim 7, characterized in that 3-methylpiperidine is employed as cyclic amine III and 2-methylglutaronitrile as dinitrile II.

9. 1,5-Bis(3-methylpiperidino)-2-methylpentane of the formula

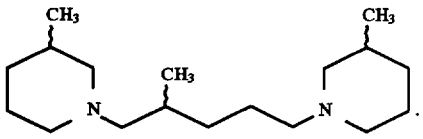

10. Process comprising using 1,5-bis(3-methylpiperidino)-2-methylpentane of the formula

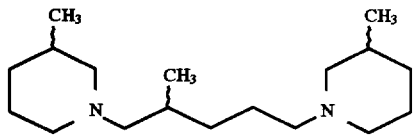

as catalyst for the production of polyurethanes, polyurethane/polyurea mixtures or polyureas in elastomer form and/or foam form.

11. Process according to claim 1, characterized in that the hydrogen pressure is greater than 10 bar.

12. Process according to claim 1, characterized in that the reaction temperature is 150° to 220° C.

13. Process according to claim 1, characterized in that the reaction with hydrogen is carried out continuously.

14. Process according to claim 1, characterized in that the dinitrile (II) which is employed is succinonitrile, glutaronitrile, adiponitrile or 2-methylglutaronitrile.

15. Process according to claim 1, characterized in that to the dinitrile II, there is added the corresponding cyclic amine of the general formula:

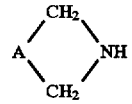

III in which A is as defined in claim 1 in a quantity of up to 2 mol per mol of dinitrile.

16. Process according to claim 6, characterized in that 3-methylpyridine is employed as cyclic amine III and 2-methylglutaronitrile as dinitrile II.

\* \* \* \* \*